US012360116B2

(12) United States Patent
Xin et al.

(10) Patent No.: US 12,360,116 B2
(45) **Date of Patent: *Jul. 15, 2025**

(54) RAPID DETECTION METHOD FOR ABRIN TOXIN

(71) Applicant: Academy of Military Medical Sciences, Beijing (CN)

(72) Inventors: Wenwen Xin, Beijing (CN); Lin Kang, Beijing (CN); Jiaxin Li, Beijing (CN); Tingting Liu, Beijing (CN); Lina Dong, Beijing (CN); Shan Gao, Beijing (CN); Jinglin Wang, Beijing (CN)

(73) Assignee: Academy of Military Medical Sciences, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/882,795

(22) Filed: Sep. 12, 2024

(65) Prior Publication Data

US 2025/0208142 A1 Jun. 26, 2025

(30) Foreign Application Priority Data

Dec. 26, 2023 (CN) ........................ 202311802616.6

(51) Int. Cl.
*G01N 33/68* (2006.01)
*G01N 21/64* (2006.01)
(Continued)

(52) U.S. Cl.
CPC ......... *G01N 33/68* (2013.01); *G01N 21/6428* (2013.01); *G01N 33/54326* (2013.01);
(Continued)

(58) Field of Classification Search
CPC ............... G01N 33/68; G01N 21/6428; G01N 33/54326; G01N 33/582
See application file for complete search history.

(56) References Cited

U.S. PATENT DOCUMENTS

2014/0065623 A1* 3/2014 Suliman .................. C12Q 1/68 435/6.12

FOREIGN PATENT DOCUMENTS

| | | | |
|---|---|---|---|
| CA | 2939124 | A1 | 8/2015 |
| CN | 102020714 | A | 4/2011 |

(Continued)

OTHER PUBLICATIONS

Liang et al. (Rapid Differential Detection of Abrin Isoforms by an Acetonitrile- and Ultrasound-Assisted on-Bead Trypsin Digestion Coupled with LC-MS/MS Analysis, oxins (Basel), May 18, 2021;13(5):358) (Year: 2021).*

(Continued)

*Primary Examiner* — Bao-Thuy L Nguyen
*Assistant Examiner* — Chau N. B. Tran
(74) *Attorney, Agent, or Firm* — Bayramoglu Law Offices LLC

(57) ABSTRACT

A rapid detection method for abrin toxin is provided. The rapid detection method for abrin toxin includes the following steps: reacting an oligonucleotide chain substrate labeled with a fluorescent group and a quenching group, a buffer solution, a BSA solution, a to-be-detected sample and sterile water, incubating at a constant temperature, detecting a fluorescence signal value, and determining whether the abrin toxin exists based on a difference between a change in final fluorescence signal value and a change in final fluorescence signal value of a negative control; where the sample is judged as a positive sample when an average value of the detected final fluorescence signal values is greater than an average value of the final fluorescence signal values of the negative control by +3 times standard deviation. According to the detection method, the direct addition of the sample into the reaction system can reach the sensitivity of 30 ng/mL.

6 Claims, 8 Drawing Sheets

Specification includes a Sequence Listing.

(51) Int. Cl.
*G01N 33/543* (2006.01)
*G01N 33/58* (2006.01)

(52) U.S. Cl.
CPC ... *G01N 33/582* (2013.01); *G01N 2021/6439* (2013.01); *G01N 2333/42* (2013.01)

(56) References Cited

FOREIGN PATENT DOCUMENTS

| | | | |
|---|---|---|---|
| CN | 112903990 | A | 6/2021 |
| CN | 113061645 | A | 7/2021 |
| CN | 117849333 | A | 4/2024 |

OTHER PUBLICATIONS

Hu Chenyi, Research on Two Novel Technologies for Toxin Detection, Acedemy of Military Science, Mster's Thesis, 2023, pp. 1-62.

Simin Fang, et al., Unimolecular Chemically Modified DNA Fluorescent Probe for One-Step Quantitative Measurement of the Activity of Human Apurinic/ Apyrimidinic Endonuclease 1 in Biological Samples, Anal. Chem. 2015, pp. 11952-11956, vol. 87.

* cited by examiner

RAPID DETECTION METHOD FOR ABRIN TOXIN

CROSS REFERENCE TO THE RELATED APPLICATIONS

This application is based upon and claims priority to Chinese Patent Application No. 202311802616.6, filed on Dec. 26, 2023, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBRZBC217_Sequence_Listing.xml, created on 08/16/2024, and is 24,405 bytes in size.

TECHNICAL FIELD

The present invention belongs to the technical field of toxin detection, and particularly relates to a rapid detection method for abrin toxin.

BACKGROUND

Abrin toxin (AT) is a toxin protein extracted from seeds of *Adenanthera pavonina* of Leguminosae. AT can be transmitted through food, water or aerosols, inhibit protein synthesis, and exert toxic effects by causing cell death through direct membrane damage, apoptotic pathways, and cytokine release. Ricin toxin (RT) has a very similar structure and biological characteristics to AT. Both RT and AT belong to a type II ribosome-inactivating protein (RIP) with N-glycosidase activity, and can specifically and irreversibly hydrolyze adenine (A4324) on the 28S rRNA of the ribosome of an organism, resulting in the inability of the ribosome to bind to an elongation factor, thereby inhibiting the translation function of the ribosome, inhibiting protein synthesis, and then exerting a toxic effect. The enzymatic activity acts on an adenine-containing oligonucleotide chain in vitro, so that adenine is shed and a base deletion (apurinic/apyrimidinic, AP) site is formed at the corresponding position.

The enzymatic activity of the toxin not only plays an important role in organisms, but also is also often used as a means of detection. Therefore, AT is usually used to establish a detection method based on its enzymatic activity, which is mainly based on its N-glycosidase activity acting on different types of adenine-containing nucleic acid substrates, and then detecting the adenine content through mass spectrometry technology. This method has the advantages of strong specificity and high sensitivity, and can detect whether RT and AT are toxic or not. However, this method usually takes about 2-5 h from incubation of the toxin and substrate to on-machine detection (the incubation time depends on the toxin content in the sample), which is time-consuming and not conducive to rapid detection. In addition, the used instrument is expensive and costly. In addition, some scholars have achieved the detection of AT by combining an electrochemical sensor, cytotoxicity and other methods, which has a narrow application scope and has not been widely promoted.

Currently, the research on the enzyme properties of AT mainly centers on the activity of N-glycosidase, and the detection method is mainly based on mass spectrometry. The development of a detection method with high specificity and sensitivity, simple operation, and rapid, accurate and efficient detection based on the enzyme properties other than N-glycosidase of AT will help reduce the detection cost, greatly shorten the detection time, achieve rapid on-site detection, and prevent or respond to emergencies timely. Therefore, the detection, identification and characterization of AT in various sample matrices are of great significance.

SUMMARY

In view of this, an objective of the present invention is to provide a rapid detection method for AT, so as to solve the problems of long time, narrow application range and low sensitivity of the detection method for AT in the prior art.

In order to achieve the above objective, the present invention provides the following technical solutions.

The present invention provides a rapid detection method for AT, which comprises the following steps:

Reacting an oligonucleotide chain substrate labeled with a fluorescent group and a quenching group, a buffer solution, a bovine serum albumin (BSA) solution, a to-be-detected sample and sterile water, incubating at a constant temperature, detecting a fluorescence signal value, and determining whether the abrin toxin exists based on a difference between an average value of final fluorescence signal values and an average value of final fluorescence signal values of a negative control; and enriching the to-be-detected sample by using antibody-coated magnetic beads.

Preferably, an amount of the oligonucleotide chain substrate labeled with the fluorescent group and the quenching group, the buffer solution, the BSA solution, the to-be-detected sample and the sterile water is 0.5-6 μL.

Preferably, a coating amount of the antibody and the magnetic beads is 20-30 μg of the antibody-coated 0.5-2 mg of the magnetic beads.

Preferably, the buffer solution comprises an ammonium formate buffer solution, an ammonium acetate buffer solution, an ammonium citrate buffer solution, an ammonium acetate+ethylene diamine tetraacetic acid (EDTA) buffer solution, or an ammonium citrate+EDTA buffer solution.

Preferably, the oligonucleotide chain substrate labeled with the fluorescent group and the quenching group has a final concentration of 2-20 M, the ammonium formate buffer solution, the ammonium acetate buffer solution and the ammonium citrate buffer solution have a final concentration of 0.2-20 mM; in the ammonium acetate+EDTA buffer solution, the ammonium acetate has a final concentration of 0.2-20 mM, and the EDTA has a final concentration of 0.2-0.8 mM; in the ammonium citrate+EDTA buffer solution, the ammonium citrate has a final concentration of 0.2-20 mM, and the EDTA has a final concentration of 0.2-0.8 mM; and the BSA solution has a final concentration of 10-100 μg/mL.

Preferably, the reaction is performed at a pH value of 3.5-4.8 and a temperature of 40-75° C. for 30-50 min.

Preferably, the fluorescence signal value is detected 2-5 times during the constant temperature incubation.

Preferably, the sample is judged as a positive sample when the average value of the detected final fluorescence signal values is greater than the average value of the final fluorescence signal values of the negative control by +3 times standard deviation.

Compared with the prior art, the present invention has the following beneficial effects:

The present invention clarifies for the first time that abrin toxin (AT) can act on a base deletion (apurinic/apyrimidinic, AP) site on the oligonucleotide chain after deadenination, has AP lyase activity, and establishes a novel AT detection method based on fluorescence signal value detection according to the enzyme activity. The reaction system of this method has simple components and only comprises a BSA solution, a buffer solution, an oligonucleotide substrate modified by a fluorescent group and a quenching group, toxin and sterile water. The reaction principle is that AT firstly exerts the N-glycosidase activity to act on adenine on an oligonucleotide chain, and then further exerts the AP lyase activity to break an oligonucleotide substrate, and simultaneously, the detection of a fluorescence signal value is performed.

The present invention designs various substrates, and establishes a rapid and efficient AT detection method by optimizing the components, concentration, substrate type, volume, reaction temperature and reaction time of the reaction system. After optimization, the detection method can complete detection only by incubation at the constant temperature of 63° C. for 40 min. The detection method of the present invention has high sensitivity, the direct addition of the sample into the reaction system can reach the sensitivity of 30 ng/mL, the detection after enrichment using antibody-coated magnetic beads can reach the sensitivity of 0.3125 ng/mL with a strong specificity, and no cross reaction exists between the toxin sample and RT.

The reaction system of the present invention has simple components and reaction conditions, short reaction time and no need for expensive detection instruments and complex professional operation, which breaks through the technical barrier of the current AT detection method, and can be used for on-site rapid screening and rapid detection of in vitro AT poisoning samples.

DETAILED DESCRIPTION OF THE EMBODIMENTS

Figure 1:
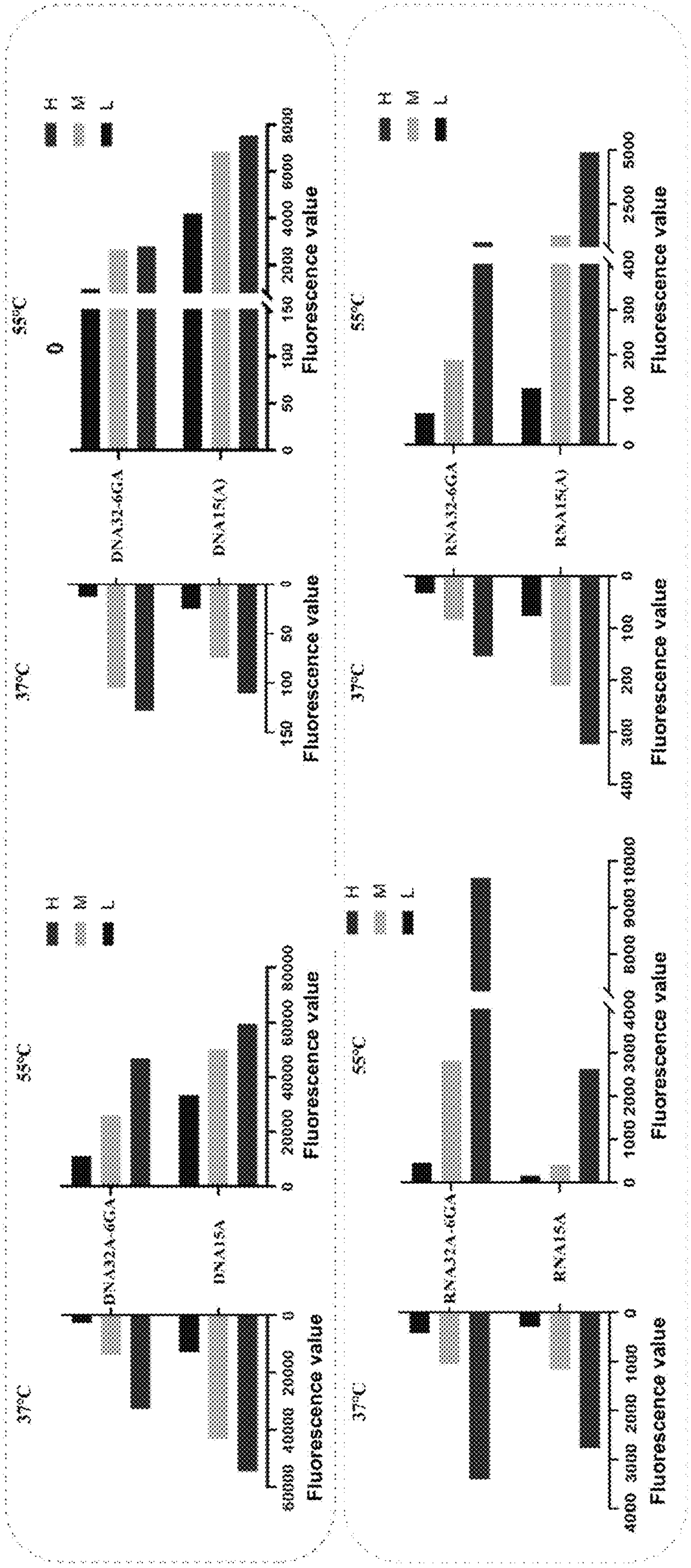
FIG. 1 is a graph showing the reaction results of AT acting on different single-stranded DNAs and single-stranded RNAs at 37° C. and 55° C. (note: H, 100 μg/mL; M, 10 μg/mL; L, 1 μg/mL)
Figure 2A:
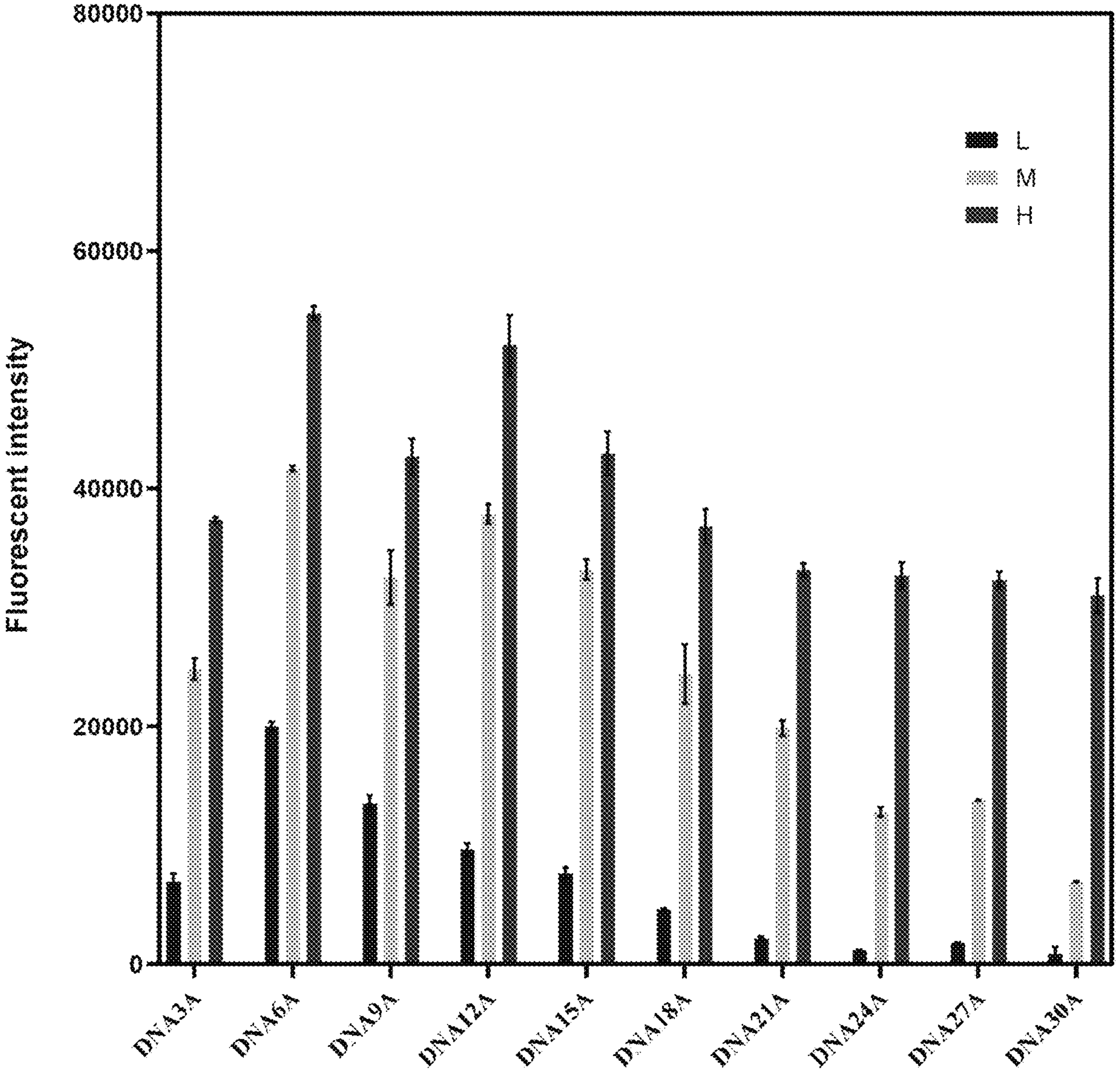
FIGS. 2A-2E are graphs showing the reaction results of various types of substrates (note: H, 100 μg/mL; M, 10 μg/mL; L, 1 μg/mL)
Figure 2B:
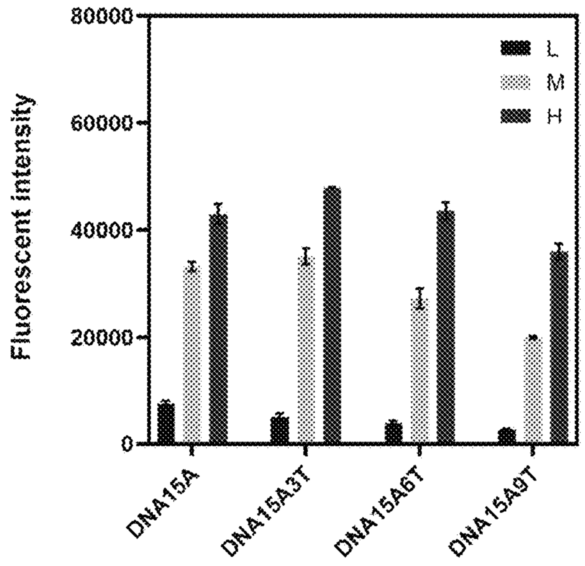
Figure 2C:
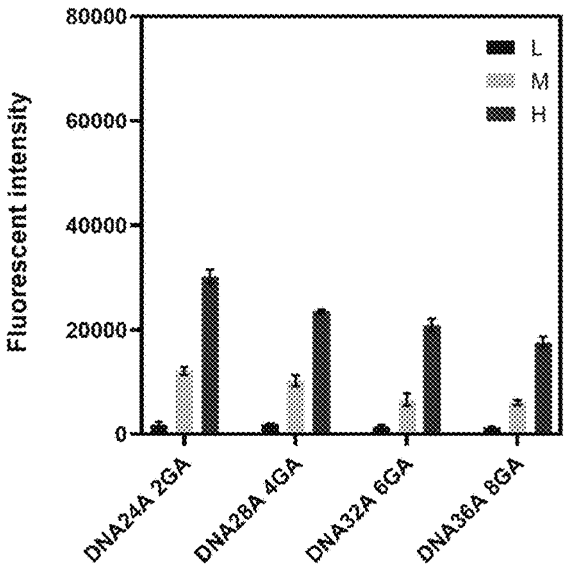
Figure 2D:
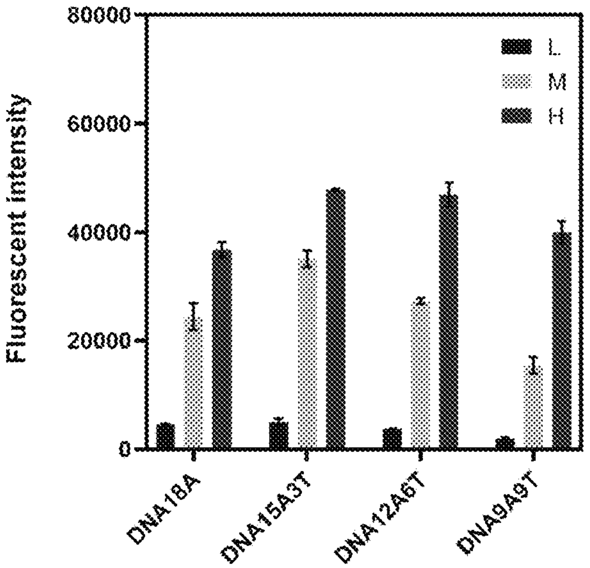
Figure 2E:
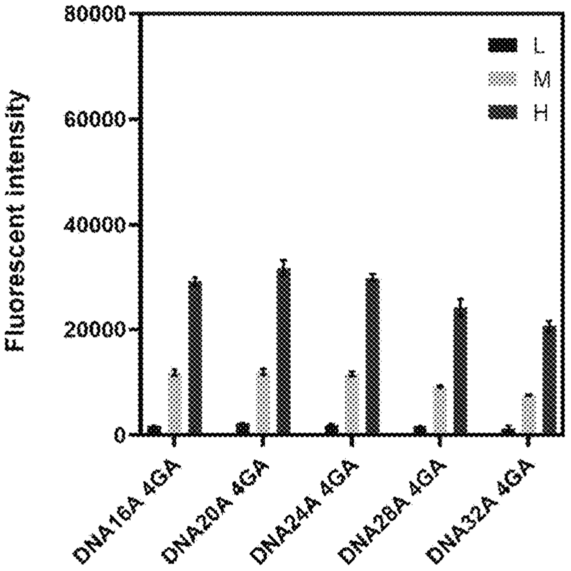
Figure 3:
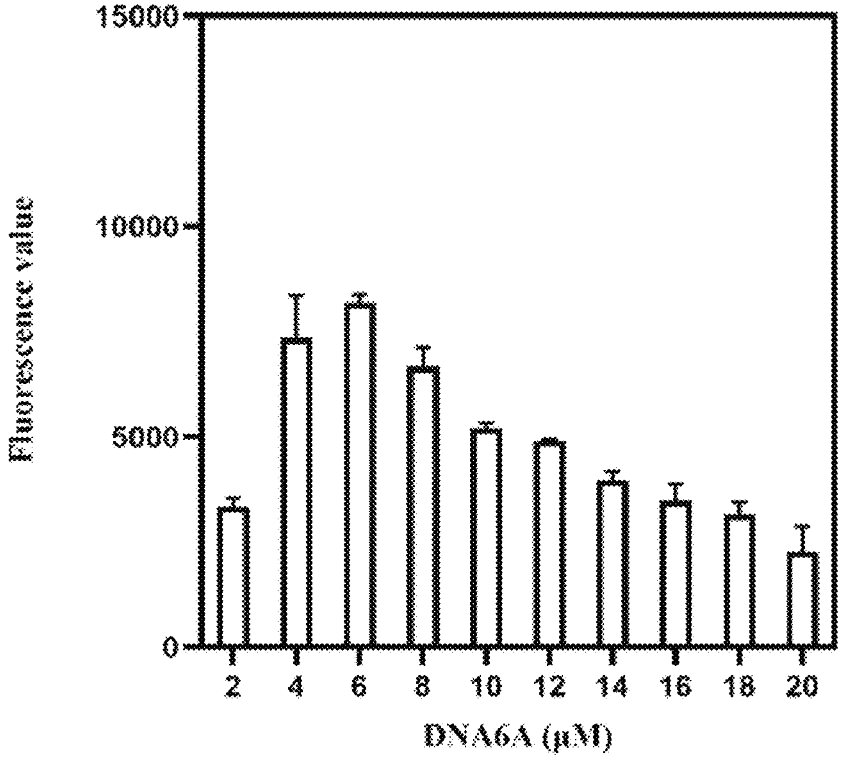
FIG. 3 is a graph showing the results of different reaction concentrations of DNA6A.
Figure 4:
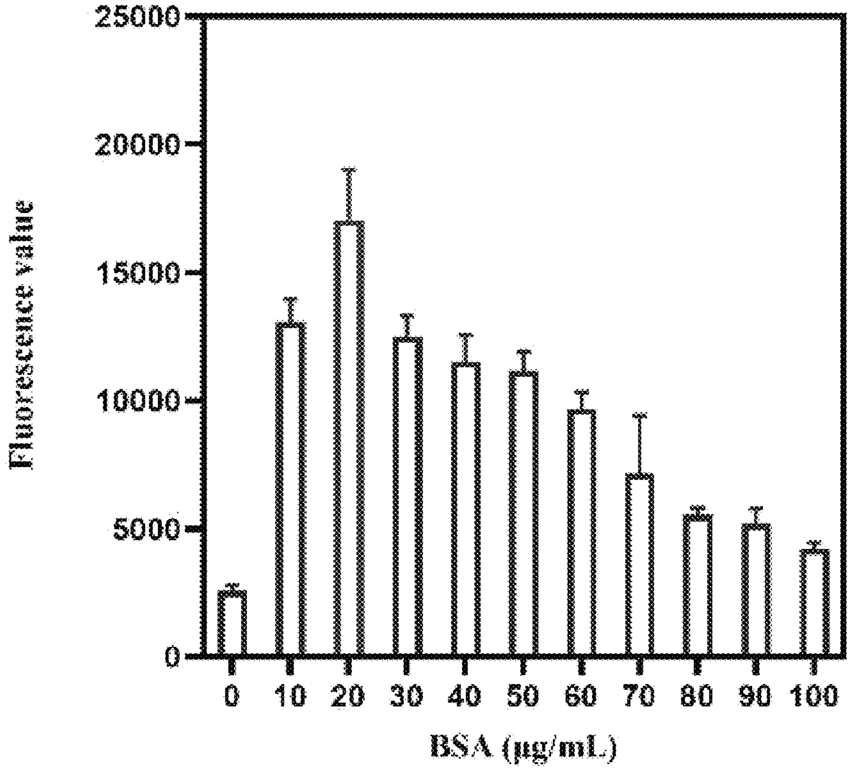
FIG. 4 is a graph showing the results of different reaction concentrations of BSA.
Figure 5A:
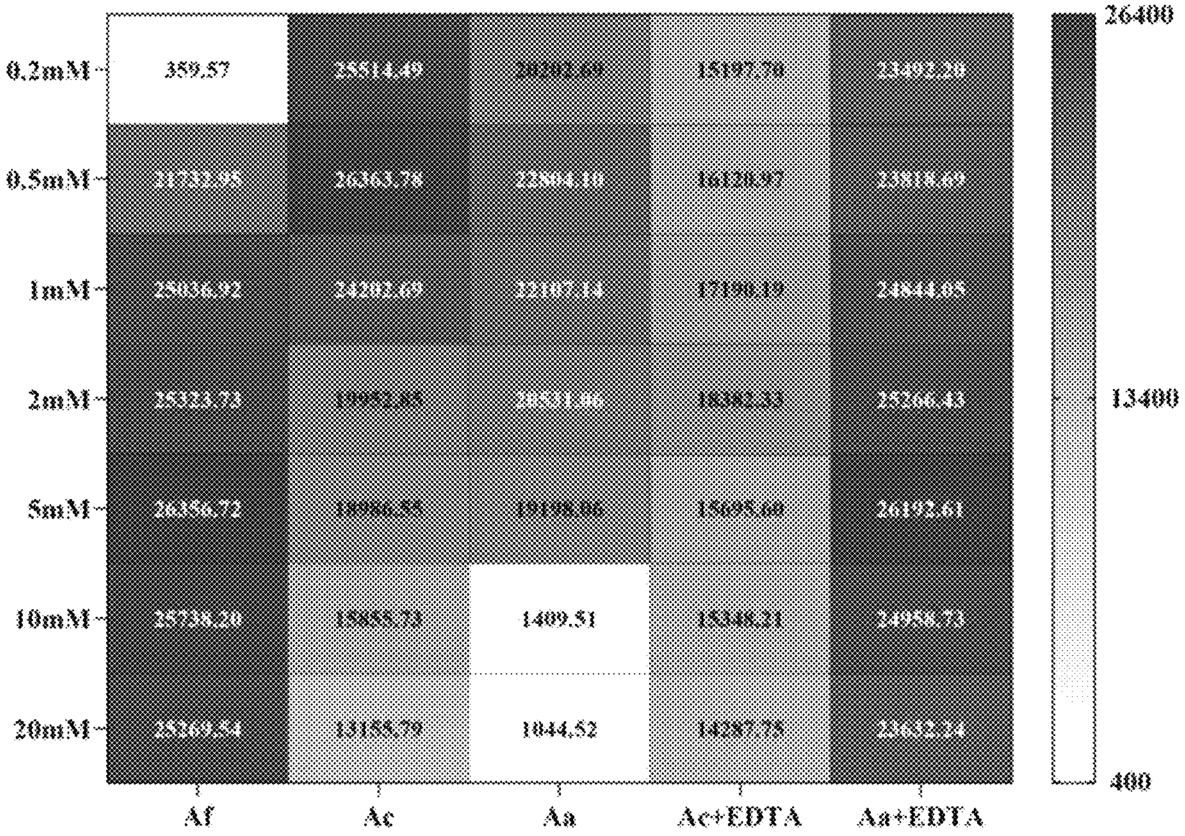
FIGS. 5A-5B are graphs showing the reaction results of different buffer solutions and optimal buffer solutions at different pH values (Af: ammonium formate buffer solution; Ac: ammonium citrate buffer solution; Aa: ammonium acetate buffer solution; Ac+EDTA: ammonium citrate+EDTA buffer solution; and Aa+EDTA: ammonium acetate+EDTA buffer solution)
Figure 5B:
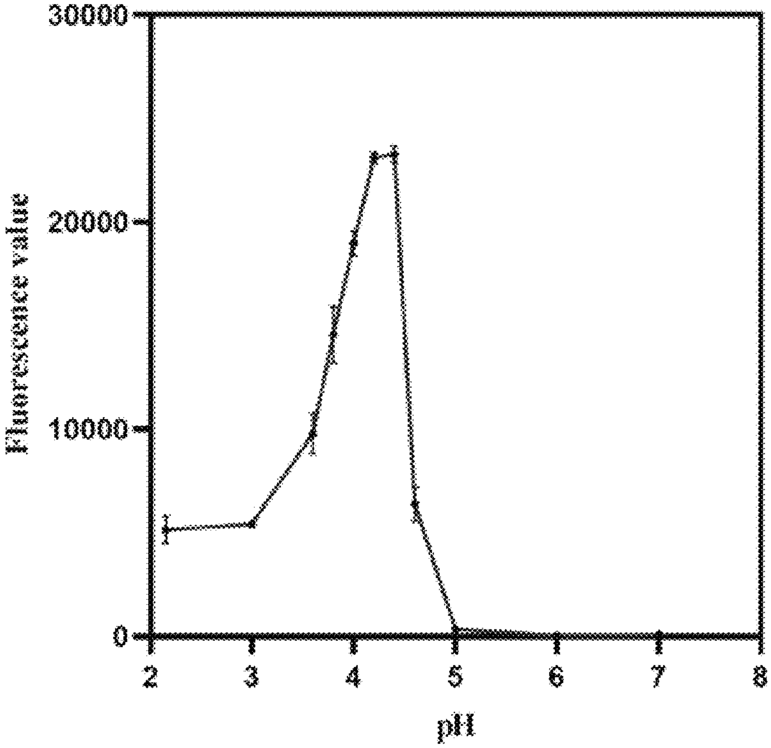

The present invention provides a rapid detection method for abrin toxin, which comprises the following steps:

An oligonucleotide chain substrate labeled with a fluorescent group and a quenching group, a buffer solution, a BSA solution, a to-be-detected sample and sterile water are reacted, the reaction system is incubated at a constant temperature, a fluorescence signal value is detected, and whether the abrin toxin exists is determined based on a difference between an average value of final fluorescence signal values and an average value of final fluorescence signal values of a negative control.

In the present invention, the oligonucleotide chain substrate is DNA15A, RNA15A, DNA15(A), RNA15(A), DNA32A-6GA, RNA32A-6GA, DNA32-6GA, and RNA32-6GA; wherein a sequence of the DNA15A is AAAAAAAAAAAAAAA (SEQ ID NO: 1, linear chain structure);

a sequence of the RNA15A is AAAAAAAAAAAAAAA (SEQ ID NO: 2, linear chain structure);

a sequence of the DNA15(A) is GCTCTGCAGTCGCTG (SEQ ID NO: 3, the linear chain structure only contains one A);

a sequence of the RNA15(A) is GCUCUGCAGU-CGCUG (SEQ ID NO: 4, the linear chain structure only contains one A);

a sequence of the DNA32A-6GA is TATATATATAGAGAGAGAGAGATATATATATA (SEQ ID NO: 5, the stem of the stem-loop structure contains A);

a sequence of the RNA32A-6GA is UAUAUAUAUA-GAGAGAGAGAGAUAUAUAUAUA (SEQ ID NO: 6, the stem of the stem-loop structure contains A);

a sequence of the DNA32-6GA is GCGCGCGCGCGAGAGAGAGAGAGCGCGCGCGC (SEQ ID NO: 7, the stem of the stem-loop structure does not contain A);

a sequence of the RNA32-6GA is GCGCGCGCGCGAGAGAGAGAGAGCGCGCGCGC (SEQ ID NO: 8, the stem of the stem-loop structure does not contain A);

DNA3A, DNA6A, DNA9A, DNA12A, DNA18A, DNA21A, DNA24A, DNA27A, DNA30A, DNA15A3T, DNA15A6T, DNA15A9T, DNA12A6T, DNA9A9T, DNA16-4GA, DNA20-4GA, DNA24-4GA, DNA28-4GA, DNA32-4GA, DNA24-2GA, DNA32A-6GA, and DNA36-8GA, wherein a sequence of the DNA3A is AAA (SEQ ID NO: 9, linear single-stranded DNA);

a sequence of the DNA6A is AAAAAA (SEQ ID NO: 10, linear single-stranded DNA);

a sequence of the DNA9A is AAAAAAAAA (SEQ ID NO: 11, linear single-stranded DNA);

a sequence of the DNA12A is AAAAAAAAAAAA (SEQ ID NO: 12, linear single-stranded DNA);

a sequence of the DNA18A is AAAAAAAAAAAAAAAAAA (SEQ ID NO: 13, linear single-stranded DNA);

a sequence of the DNA21A is AAAAAAAAAAAAAAAAAAAAA (SEQ ID NO: 14, linear single-stranded DNA);

a sequence of the DNA24A is AAAAAAAAAAAAAAAAAAAAAAAA (SEQ ID NO: 15, linear single-stranded DNA);

a sequence of the DNA27A is AAAAAAAAAAAAAAAAAAAAAAAAAAA (SEQ ID NO: 16, linear single-stranded DNA);

a sequence of the DNA30A is AAAAAAAAAAAAAAAAAAAAAAAAAAAAAA (SEQ ID NO: 17, linear single-stranded DNA);

a sequence of the DNA15A3T is TAAAAAAAATAAAAAAAT (SEQ ID NO: 18, with a constant number of A and an increased number of T);

a sequence of the DNA15A6T is TAAATAAATAAATAAATAAAT (SEQ ID NO: 19, with a constant number of A and an increased number of T);

a sequence of the DNA15A9T is TAATAATAATAATAATAATATAAT (SEQ ID NO: 20, with a constant number of A and an increased number of T);

a sequence of the DNA15A3T is TAAAAAAAATAAAAAAAT (SEQ ID NO: 18, with an unchanged length and an increased number of T);

a sequence of the DNA12A6T is TAAATAAATAATAATAAT (SEQ ID NO: 21, with an unchanged length and an increased number of T);

a sequence of the DNA9A9T is TATATATATATATATAAT (SEQ ID NO: 22, with an unchanged length and an increased number of T);

a sequence of the DNA16-4GA is TATAGAGAGAGA-TATA (SEQ ID NO: 23, the loop size of the stem-loop structure remains unchanged while the stem length increases);

a sequence of the DNA20-4GA is TATATAGAGAGAGATATATA (SEQ ID NO: 24, the loop size of the stem-loop structure remains unchanged while the stem length increases);

a sequence of the DNA24-4GA is TATATATAGAGAGAGATATATATA (SEQ ID NO: 25, the loop size of the stem-loop structure remains unchanged while the stem length increases);

a sequence of the DNA28-4GA is TATATATATAGAGAGAGATATATATATA (SEQ ID NO: 26, the loop size of the stem-loop structure remains unchanged while the stem length increases);

a sequence of the DNA32-4GA is TATATATATATAGAGAGAGATATATATATATA (SEQ ID NO: 27, the loop size of the stem-loop structure remains unchanged while the stem length increases);

a sequence of the DNA24-2GA is TATATATATAGAGA-TATATATATA (SEQ ID NO: 28, the stem length of the stem-loop structure remains unchanged while the loop size increases);

a sequence of the DNA28-4GA is TATATATATAGAGAGAGATATATATATA (SEQ ID NO: 26, the stem length of the stem-loop structure remains unchanged while the loop size increases);

a sequence of the DNA32A-6GA is TATATATATAGAGAGAGAGAGATATATATATA (SEQ ID NO: 5, the stem length of the stem-loop structure remains unchanged while the loop size increases); and a sequence of the DNA36-8GA is TATATATATAGAGAGAGAGAGAGAGA-TATATATATA (SEQ ID NO: 29, the stem length of the stem-loop structure remains unchanged while the loop size increases).

The to-be-detected sample is enriched by using antibody-coated magnetic beads.

In the present invention, the fluorescent group is preferably a FAM fluorescent group; the quenching group is preferably a BHQ1 quenching group; the coating amount of the antibody and the magnetic beads is preferably 20-30 μg of the antibody-coated 0.5-2 mg of the magnetic beads, more preferably 22-28 μg of antibody-coated 0.8-1.8 mg of magnetic beads, and further preferably 25 μg of antibody-coated 1 mg of magnetic beads; the use amount of the magnetic beads of each to-be-detected sample is preferably 40-60 μg, more preferably 42-58 μg, and further preferably 50 μg; the amount of the oligonucleotide chain substrate labeled with the fluorescent group and the quenching group, the buffer solution, the BSA solution, the to-be-detected sample and the sterile water is preferably 0.5-6 μL, more preferably 0.8-5 μL, and further preferably 1 μL; the buffer solution comprises an ammonium formate buffer solution, an ammonium acetate buffer solution, an ammonium citrate buffer solution, an ammonium acetate+EDTA buffer solution, or an ammonium citrate+EDTA buffer solution, and the buffer solution is preferably the ammonium citrate buffer solution; the final concentration of the oligonucleotide chain substrate labeled with the fluorescent group and the quenching group is preferably 2-20 μM, more preferably 4-15 μM, and further preferably 6 μM; the final concentration of the ammonium formate buffer solution, the ammonium acetate buffer solution and the ammonium citrate buffer solution is 0.2-20 mM, preferably 0.3-18 mM and more preferably 0.5 mM; in the ammonium acetate+EDTA buffer solution, the final concentration of the ammonium acetate is preferably 0.2-20 mM, more preferably 0.3-18 mM and further preferably 0.5 mM, and the final concentration of the EDTA is 0.2-0.8 mM, preferably 0.3-0.7 mM and more preferably 0.5 mM; in the ammonium citrate+EDTA buffer solution, the final concentration of the ammonium citrate is 0.2-20 mM, preferably 0.3-18 mM and more preferably 0.5 mM, and the final concentration of the EDTA is 0.2-0.8 mM, preferably 0.3-0.7 mM and more preferably 0.5 mM; the final concentration of the BSA solution is preferably 10-100 μg/mL, more preferably 15-80 μg/mL, and further preferably 20 μg/mL; the pH value of the reaction is preferably 3.5-4.8, more preferably 3.8-4.6, and further preferably 4.4; the reaction temperature is preferably 40-75° C., more preferably 50-70° C., and further preferably 63° C.; the reaction time is preferably 30-50 min, more preferably 35-45 min, and further preferably 40 min; the fluorescence signal value is preferably detected 2-5 times during the constant temperature incubation, and more preferably 4 times; and the sample is judged as a positive sample when the average value of the detected final fluorescence signal values is greater than the average value of the final fluorescence signal values of the negative control by +3 times standard deviation.

The technical solutions provided by the present invention will be described in detail below with reference to examples, which, however, should not be construed as limiting the scope of the present invention.

Main Reagents and Instruments:

(1) Main Reagents

Dynabeads™ antibody coupling kit (14311D): Thermo Fisher Scientific Inc.; bovine serum albumin (B2064), ammonium citrate (25102), ammonium formate (70221), and ammonium acetate (73594): Sigma-Aldrich; 0.5 M EDTA (pH 8.0) (E1170): Beijing Solarbio Science & Technology Co., Ltd.; and all oligonucleotide substrates are synthesized by GenScript Biotech Corporation.

(2) Main Instruments

Biological safety cabinet: NUAIRE, USA; Vortex mixer: Haimen Kylin-Bell Lab Instruments Co., Ltd., Jiangsu; PCR workstation (Air Clean600 PCR Workstation): AirClean Systems, USA;

HulaMixer™ sample mixer (15920D): Thermo Fisher Scientific Inc.; and real-time fluorescence quantitative PCR instrument: Life Sciences of Analytik Jena AG, Germany.

Example 1

Design and Synthesis of Different Types of Oligonucleotide Chain Substrates Related to the Experiment:

Various types of oligonucleotide chain substrates were designed, including linear chain and stem-loop structures with different lengths and different adenine contents, and the 5' terminus and the 3' terminus of all the oligonucleotide chains were labeled with FAM fluorescent group and BHQ1 quenching group and were synthesized by GenScript Biotech Corporation. The sequence information of different types of oligonucleotide chain substrates is shown in Table 1.

TABLE 1

Sequence information of different types of oligonucleotide chain substrates

| Name | Sequence | Note |
|---|---|---|
| DNA15A | FAM-AAAAAAAAAAAAAAA-BHQ1 (SEQ ID NO: 1) | Linear chain structure |
| RNA15A | FAM-AAAAAAAAAAAAAAA-BHQ1 (SEQ ID NO: 2) | Linear chain structure |
| DNA15(A) | FAM-GCTCTGCAGTCGCTG-BHQ1 (SEQ ID NO: 3) | The linear chain structure only contains one A |
| RNA15(A) | FAM-GCUCUGCAGUCGCUG-BHQ1 (SEQ ID NO: 4) | The linear chain structure only contains one A |
| DNA32A-6GA | FAM-TATATATATAGAGAGAGAGAGATATATATATA-BHQ1 (SEQ ID NO: 5) | The stem of the stem-loop structure contains A |
| RNA32A-6GA | FAM-UAUAUAUAUAGAGAGAGAGAGAUAUAUAUAUA-BHQ1 (SEQ ID NO: 6) | The stem of the stem-loop structure contains A |
| DNA32-6GA | FAM-GCGCGCGCGCGAGAGAGAGAGAGCGCGCGCGC-BHQ1 (SEQ ID NO: 7) | The stem of the stem-loop structure does not contain A |
| RNA32-6GA | FAM-GCGCGCGCGCGAGAGAGAGAGAGCGCGCGCGC-BHQ1 (SEQ ID NO: 8) | The stem of the stem-loop structure does not contain A |

Example 2

Verification of AP Lyase Activity:

100 μg/mL, 10 μg/mL and 1 μg/mL of AT were used to act on the different types of oligonucleotide chain substrates designed in Example 1 (see Table 1 for details), and sterile water was taken as a negative control, reactions were performed at 37° C. and 55° C. to explore whether AT had AP lyase activity. The reaction system was 30 μL in volume and was composed of 6 μL of ammonium formate buffer solution, 6 μL of BSA solution, 6 μL of substrate, 6 μL of AT and 6 μL of sterile water. The used buffer solution was 20 mM ammonium formate buffer solution, the final concentration of the substrate was 10 μM, and the final concentration of BSA was 50 μg/mL. After the reaction system was prepared and the corresponding concentration of AT/sterile water was added for reaction, the reaction system was placed in a qPCR instrument for incubation at a constant temperature, the instrument was set as FAM channel fluorescence signal acquisition, and fluorescence signal value detection was performed in the first step for 72 cycles, wherein the cycle conditions were 5 s in the first step and 9 min in the second step for 55 s. After the reaction was completed, the original data obtained by the detection of the instrument was processed, and the difference between the change in the fluorescence signal value after three different concentrations of AT acted on the same substrate after 72 cycles and the change in the fluorescence signal value of the negative control was compared.

The experimental results are shown in FIG. 1. It can be seen from FIG. 1 that AT can act on single-stranded DNA substrates as well as single-stranded RNA substrates, both of which can cleave the corresponding substrate at the formed AP site; under the same reaction conditions, the response value of the fluorescence signal of the AT acting on the single-stranded DNA substrate is significantly higher than that of the corresponding single-stranded RNA substrate, and the more the adenine contained in the single-stranded DNA substrate, the higher the response value of the generated fluorescence signal; and when the AT acts on the same substrate, the response value of the fluorescence signal at the temperature of 55° C. is significantly higher than that at the temperature of 37° C.

Example 3

Optimization of Reaction Substrates:

A DNA substrate was selected as an optimization object, and 25 μg/mL AT was used to act on different types of stem-loop structures and linear single-stranded DNA substrates (specific sequence information is shown in Table 2), and sterile water was used as a negative control. The reactions were performed at 55° C. The reaction system was 5 μL in volume and was composed of 1 μL of ammonium citrate buffer solution at 0.5 mM, 1 μL of BSA solution at 50 μg/mL, 1 μL of substrate at 10 μM, 1 μL of AT and 1 μL of sterile water. After the reaction system was prepared and reacted, the reaction system was placed in a qPCR instrument for incubation at a constant temperature, the instrument was set as FAM channel fluorescence signal acquisition, and fluorescence signal value detection was performed in the first step for 4 cycles, wherein the cycle conditions were 5 s in the first step and 9 min in the second step for 55 s. After the reaction was completed, the original data obtained by the detection of the instrument was processed, the difference between the change in the fluorescence signal value after three different concentrations of AT acted on the same substrate after 4 cycles and the change in the fluorescence signal value of the negative control was compared, and the optimal reaction substrate was selected.

TABLE 2

Sequence information of single-stranded DNA substrates of different lengths for substrate optimization

| Name | Sequence | Note |
|---|---|---|
| DNA3A | FAM-AAA-BHQ1 (SEQ ID NO: 9) | Linear |
| DNA6A | FAM-AAAAAA-BHQ1 (SEQ ID NO: 10) | single-stranded |
| DNA9A | FAM-AAAAAAAAA-BHQ1 (SEQ ID NO: 11) | DNA |
| DNA12A | FAM-AAAAAAAAAAAA-BHQ1 (SEQ ID NO: 12) | |
| DNA15A | FAM-AAAAAAAAAAAAAAA-BHQ1 (SEQ ID NO: 1) | |
| DNA18A | FAM-AAAAAAAAAAAAAAAAAA-BHQ1 (SEQ ID NO: 13) | |
| DNA21A | FAM-AAAAAAAAAAAAAAAAAAAAA-BHQ1 (SEQ ID NO: 14) | |
| DNA24A | FAM-AAAAAAAAAAAAAAAAAAAAAAAA-BHQ1 (SEQ ID NO: 15) | |
| DNA27A | FAM-AAAAAAAAAAAAAAAAAAAAAAAAAAA-BHQ1 (SEQ ID NO: 16) | |
| DNA30A | FAM-AAAAAAAAAAAAAAAAAAAAAAAAAAAAAA-BHQ1 (SEQ ID NO: 17) | |
| DNA15A3T | FAM-TAAAAAAAATAAAAAAAT-BHQ1 (SEQ ID NO: 18) | The number of A |
| DNA15A6T | FAM-TAAATAAATAAATAAATAAAT-BHQ1 (SEQ ID NO: 19) | is unchanged |
| DNA15A9T | FAM-TAATAATAATAATAATAATATAAT-BHQ1 (SEQ ID NO: 20) | The number of T increases |
| DNA15A3T | FAM-TAAAAAAAATAAAAAAAT-BHQ1 (SEQ ID NO: 18) | The length is |
| DNA12A6T | FAM-TAAATAAATAATAATAAT-BHQ1 (SEQ ID NO: 21) | unchanged |
| DNA9A9T | FAM-TATATATATATATATAAT-BHQ1 (SEQ ID NO: 22) | The number of T |
| DNA16-4GA | FAM-TATAGAGAGAGATATA-BHQ1 (SEQ ID NO: 23) | increases |
| DNA20-4GA | FAM-TATATAGAGAGAGATATATA-BHQ1 (SEQ ID NO: 24) | Stem-loop |
| DNA24-4GA | FAM-TATATATAGAGAGAGATATATATA-BHQ1 (SEQ ID NO: 25) | structure |
| DNA28-4GA | FAM-TATATATATAGAGAGAGATATATATATA-BHQ1 (SEQ ID NO: 26) | The ring size is unchanged |
| DNA32-4GA | FAM-TATATATATATAGAGAGAGATATATATATATA-BHQ1 (SEQ ID NO: 27) | The stem length increases |
| DNA24-2GA | FAM-TATATATATAGAGATATATATATA-BHQ1 (SEQ ID NO: 28) | Stem-loop |
| DNA28-4GA | FAM-TATATATATAGAGAGAGATATATATATA-BHQ1 (SEQ ID NO: 26) | structure The stem length |
| DNA32A-6GA | FAM-TATATATATAGAGAGAGAGAGATATATATATA-BHQ1 (SEQ ID NO: 5) | is unchanged The loop size |
| DNA36-8GA | FAM-TATATATATAGAGAGAGAGAGAGAGATATATATATA-BHQ1 (SEQ ID NO: 29) | increases |

The experimental results are shown in FIGS. 2A-2E. It can be seen from FIGS. 2A-2E that DNA6A in the linear single-stranded DNA substrates is the optimal substrate for the reaction.

Example 4

Optimization of Reaction Components:

DNA6A was selected as the optimal reaction substrate, the optimal reaction concentration of the reaction substrate and the optimal reaction concentration of BSA were explored, and the reaction effects of the ammonium formate buffer solution, the ammonium acetate buffer solution, the ammonium citrate buffer solution, the ammonium acetate+EDTA buffer solution and the ammonium citrate+EDTA buffer solution with different concentrations were compared. The substrate concentrations were 2 μM, 4 μM, 6 μM, 8 μM, 10 PM, 12 μM, 14 μM, 16 μM, 18 μM, and 20 μM, and the BSA concentrations were 10 μg/mL, 20 μg/mL, 30 μg/mL, 40 μg/mL, 50 μg/mL, 60 μg/mL, 70 μg/mL, 80 μg/mL, 90 μg/mL, and 100 μg/mL. The concentration gradient of various buffer solutions was 0.2 mM, 0.5 mM, 1 mM, 2 mM, 5 mM, 10 mM, and 20 mM, and the pH was 4.0. After the optimal reaction buffer solution and the reaction concentration thereof were determined, the optimal reaction pH of the buffer solution was explored, including pH 2.15, pH 3, pH 3.6, pH 3.8, pH 4.0, pH 4.2, pH 4.4, pH 4.6, pH 5, pH 6, and pH 7. The sterile water was used as a negative control in all reactions, the reaction temperature was 55° C., the volume of the reaction system was 5 μL, and the system was composed of 1 μL of the buffer solution, 1 μL of the BSA solution, 1 μL of the substrate, 1 μL of AT and 1 μL of sterile water. After the reaction system was prepared and reacted, the reaction system was placed in a qPCR instrument for incubation at a constant temperature, the instrument was set as FAM channel fluorescence signal acquisition, and fluorescence signal value detection was performed in the first step for 4 cycles, wherein the cycle conditions were 5 s in the first step and 9 min in the second step for 55 s. After the reaction was completed, the original data obtained by the detection of the instrument was processed, and the difference between the change in the fluorescence signal value after AT acted on the substrate after 4 cycles and the change in the fluorescence signal value of the negative control was compared.

The experimental results are shown in FIGS. 3-5B. It can be seen from FIGS. 3-5B that the optimal reaction concentration of DNA6A is 6 μM, the optimal reaction concentration of BSA is 20 μg/mL, the optimal reaction buffer solution is 0.5 mM of the ammonium citrate buffer solution, and the optimal reaction pH value is 4.4.

Example 5

Optimization of Reaction System Volume and Reaction Temperature:

The optimal volume and the optimal reaction temperature of the reaction system were explored. First, 100 μg/mL, 10 μg/mL and 1 μg/mL of AT were used, and sterile water was used as a negative control. The reaction was performed at 55° C., and the reaction system volumes were 5 μL, 10 μL, 15 μL, 20 μL, 25 μL, and 30 μL. The system was composed of 0.5 mM of the ammonium citrate buffer solution at the pH value of 4.4, 20 μg/mL of the BSA solution, 6 μM of the substrate, the corresponding concentration of AT and the sterile water. Then, the reaction was performed at 43.4° C., 47° C., 51° C., 55° C., 59° C., 63° C., 67° C. and 70.6° C. using 25 μg/mL of AT and the reaction system volume of 5 μL.

Figure 6:
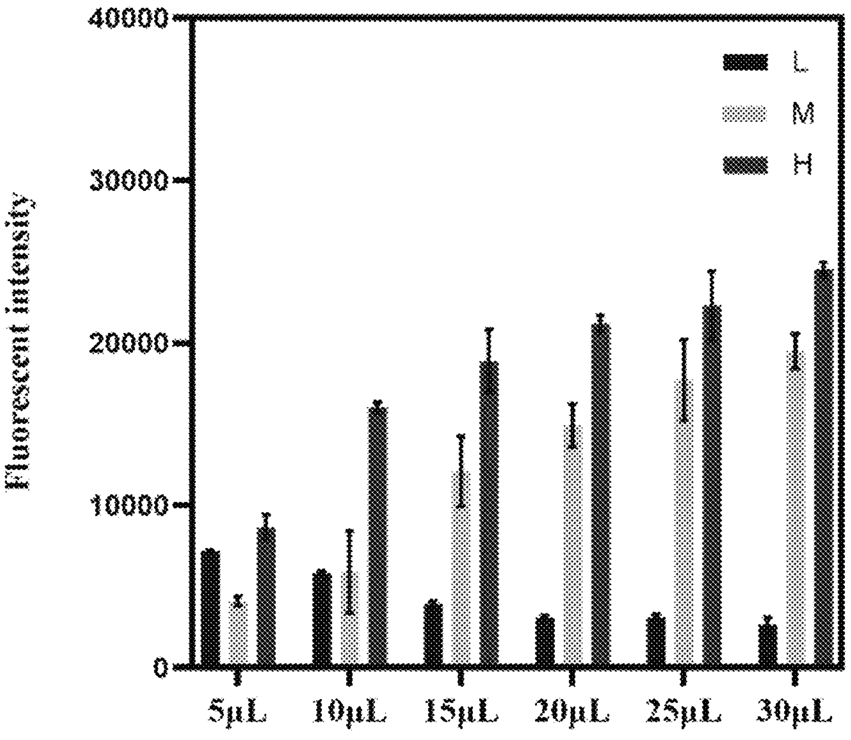
FIG. 6 is a graph showing the reaction results of different reaction system volumes (note: H, 100 μg/mL; M, 10 μg/mL; L, 1 μg/mL)
Figure 7:
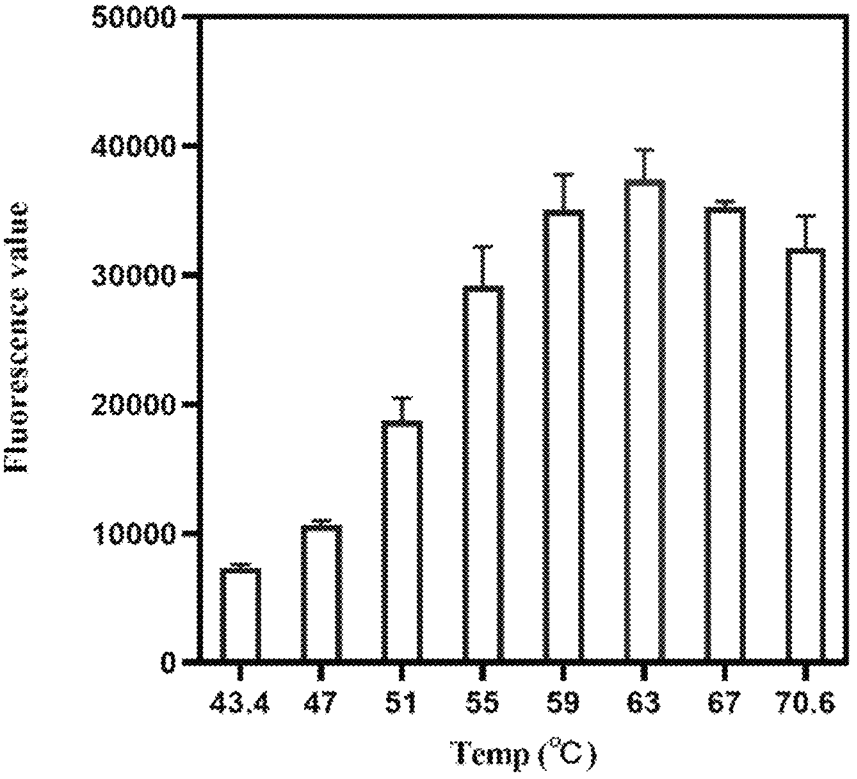
FIG. 7 is a graph showing the reaction results at different reaction temperatures.

The experimental results are shown in FIGS. 6-7. It can be seen from FIGS. 6-7 that when the reaction system volume is 5 μL, the fluorescence signal value in the AT reaction at a low concentration has the highest response intensity, and therefore, 5 μL is selected as the optimal reaction system volume. When the reaction temperature is 63° C., the fluorescence signal value has the highest intensity, and therefore, 63° C. is selected as the optimal reaction temperature.

Example 6

Optimization of Detection Sensitivity after Direct Addition of the Samples into the Reaction System:

The sample enrichment was performed without using antibody-coated magnetic beads, and the detection sensitivity of the detection method was explored by using an optimized reaction system. The sterile water was used as a negative control, and the reaction was performed at 63° C. The concentrations of AT were set to 0.1 μg/mL, 0.06 μg/mL, 0.03 μg/mL, and 0.01 μg/mL, and the reaction system volume was 5 μL, and the system was composed of 1 μL of 0.5 mM ammonium citrate buffer solution at pH 4.4, 1 μL of 20 μg/mL BSA solution, 1 μL of 6 μM substrate DNA6A, 1 μL of AT, and 1 μL of sterile water. After the reaction system was prepared and reacted, the reaction system was placed in a qPCR instrument for incubation at a constant temperature, the instrument was set as FAM channel fluorescence signal acquisition, and fluorescence signal value detection was performed in the first step for 4 cycles, wherein the cycle conditions were 5 s in the first step and 9 min in the second step for 55 s. After the reaction was completed, the original data obtained by the detection of the instrument was processed, and the final fluorescence signal value after different concentrations of AT acted on the same substrate after 4 cycles was compared with the final fluorescence signal value of the negative control. The sample was judged as a positive sample when the average value of the final fluorescence signal values of the sample was greater than the average value of the final fluorescence signal values of the negative control by +3 times standard deviation.

Figure 8:
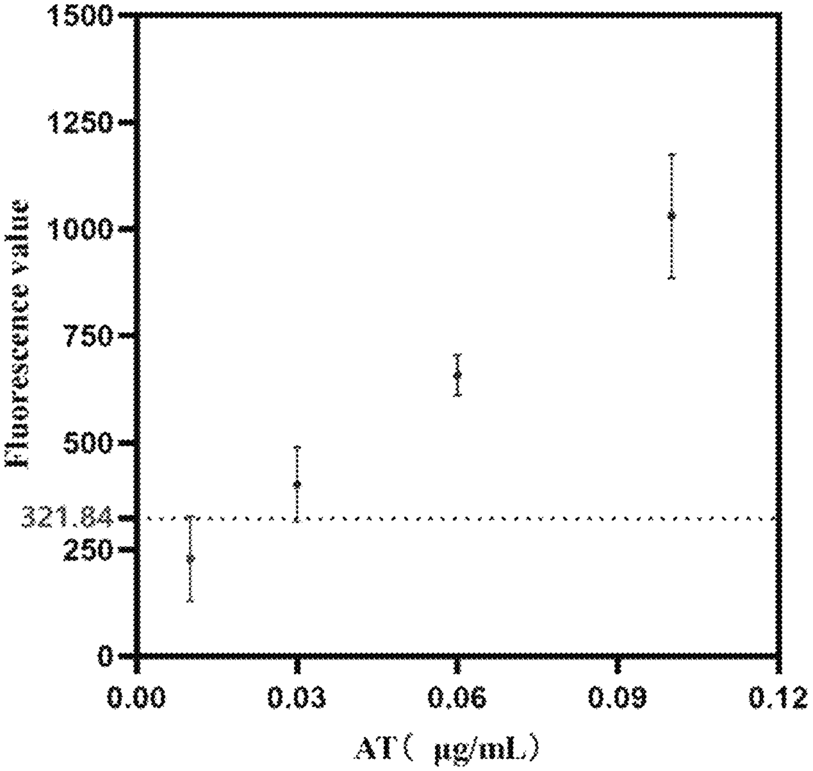
FIG. 8 is a graph showing the detection sensitivity results of AT without adding magnetic beads.

The experimental results are shown in FIG. 8. It can be seen from FIG. 8 that the detection sensitivity of AT is 30 ng/mL.

Example 7

Optimization of Detection Sensitivity of the Reaction System after Sample Enrichment by Antibody-Coated Magnetic Beads:

The sample enrichment was performed using antibody-coated magnetic beads, the coating amount of the antibody and the magnetic beads was 25 μg of the antibody-coated 1 mg of the magnetic beads, and 50 μg of magnetic beads was used for each sample. The sample volume was 500 μL. After incubation with the corresponding magnetic beads at room temperature for 1 h, the sample was adsorbed by a magnetic rack for 1 min, and the supernatant was removed. Then, the reaction system optimized in Example 4 and Example 5 was added, and the mixture was gently pipetted and incubated at 63° C. for 40 min. The concentrations of AT were set to 10 ng/mL, 5 ng/mL, 2.5 ng/mL, 1.25 ng/mL, 0.625 ng/mL, and 0.3125 ng/mL, and sterile water was used as a negative control to explore the reaction system and the detection sensitivity of the detection method. The specificity of the reaction system was verified using 10 ng/mL of RT samples.

Figure 9:
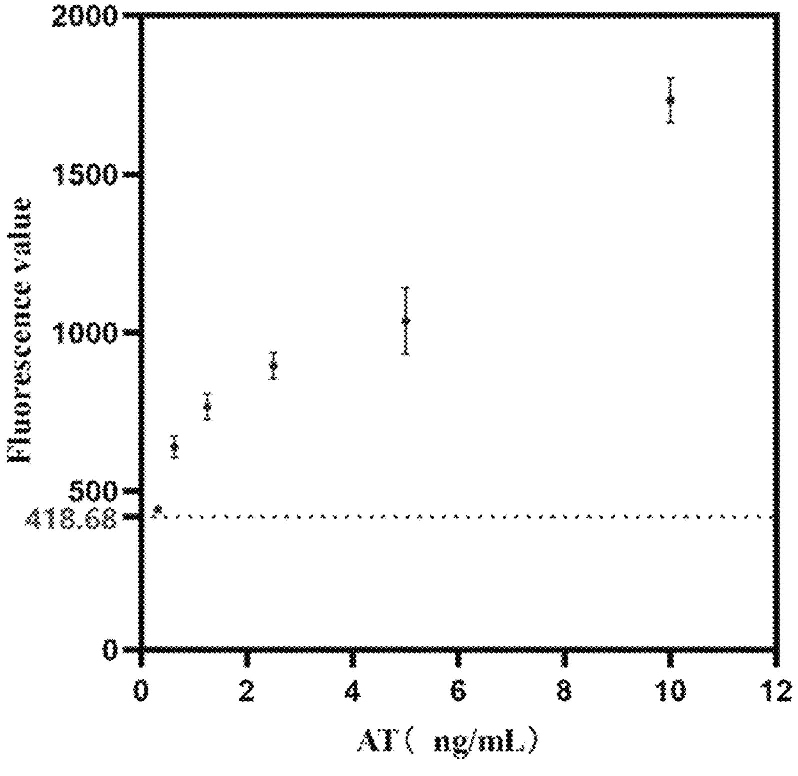
FIG. 9 is a graph showing the detection sensitivity results of AT with adding magnetic beads.
Figure 10:
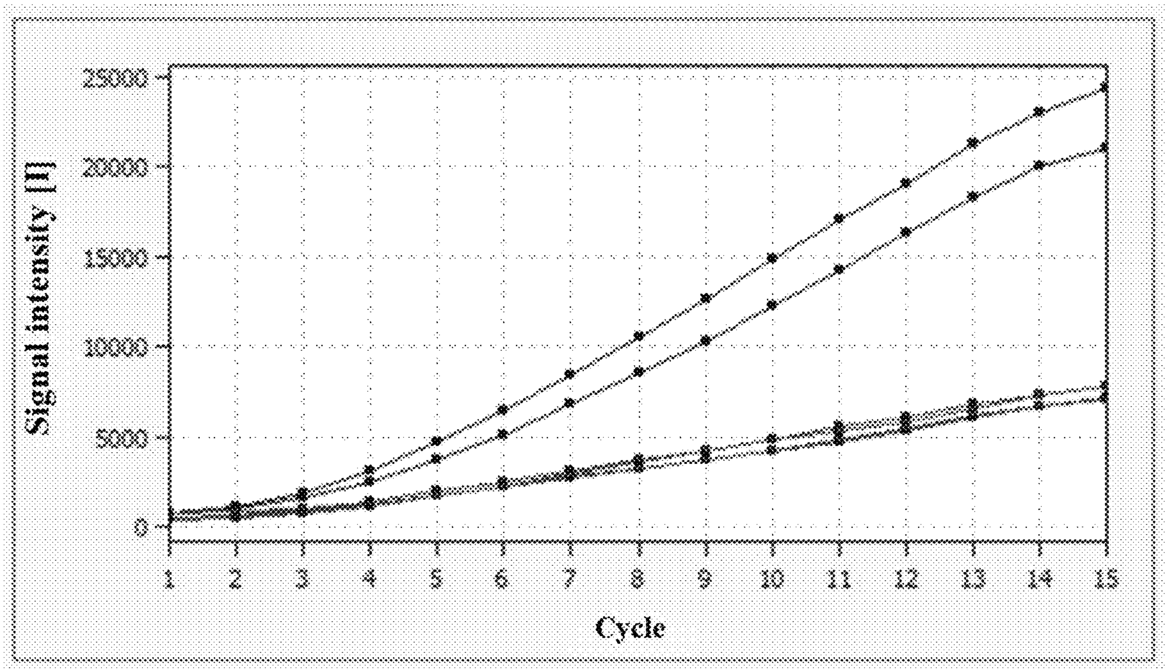
FIG. 10 is a graph showing the results of specificity verification (blue: AT sample 10 ng/mL; green: RT sample 10 ng/mL; red: negative sample).

The experimental results are shown in FIGS. 9-10. It can be seen from FIGS. 9-10 that the detection method has good specificity, no cross reaction with RT occurs, and the detection sensitivity can reach 0.3125 ng/mL, which is about 96 times higher than that before the magnetic beads are used.

It can be seen from the above examples that the reaction system of the present invention is 1 μL of 0.5 mM ammonium citrate buffer solution, 1 μL of 20 μg/mL BSA solution, 1 μL of 6 μM DNA6A substrate, 1 μL of AT and 1 μL of sterile water, and when the sample is directly added to the reaction system, the detection can be completed by constant-temperature incubation at pH 4.4 and 63° C. for 40 min. According to the detection method of the present invention, the direct addition of the toxin sample into the reaction system can reach the sensitivity of 30 ng/mL, the detection after enrichment using antibody-coated magnetic beads can reach the sensitivity of 0.3125 ng/mL with a strong specificity, and no cross reaction exists between the toxin sample and abrin toxin.

The above descriptions are only preferred embodiments of the present invention. It should be noted that those of ordinary skill in the art can also make several improvements and modifications without departing from the principle of the present invention, and such improvements and modifications shall fall within the protection scope of the present invention.

What is claimed is:

1. A rapid detection method for abrin toxin, comprising the following steps:

subjecting an adenine-containing oligonucleotide chain substrate labeled with a fluorescein (FAM) fluorescent group and a Black Hole Quencher 1 (BHQ1) quenching group, a buffer solution, a bovine serum albumin (BSA) solution, a to-be-detected sample, and sterile water to a reaction to obtain a product, incubating the product at a constant temperature to obtain an incubated product, detecting a fluorescence signal value 2-5 times to obtain final fluorescence signal values of the incubated product, and determining whether the abrin toxin exists based on a difference between an average value of final fluorescence signal values of the incubated product and a final fluorescence signal value of a negative control; wherein the buffer solution is an ammonium formate buffer solution, an ammonium acetate buffer solution, an ammonium citrate buffer solution, an ammonium acetate and ethylene diamine tetraacetic acid (EDTA) buffer solution, or an ammonium citrate and EDTA buffer solution;

the to-be-detected sample is enriched by using antibody-coated magnetic beads, wherein antibodies for coating the magnetic beads are specific for abrin toxin; and the negative control is sterile water.

2. The rapid detection method according to claim 1, wherein an amount of the adenine-containing oligonucleotide chain substrate labeled with the FAM fluorescent group and the BHQ1 quenching group, the buffer solution, the BSA solution, the to-be-detected sample, and the sterile water is 0.5-6 μL, respectively.

3. The rapid detection method according to claim 1, wherein an amount of the antibodies for coating the magnetic beads is 20-30 μg per 0.5-2 mg of the magnetic beads.

4. The rapid detection method according to claim 1, wherein the adenine-containing oligonucleotide chain substrate labeled with the FAM fluorescent group and the BHQ1 quenching group has a final concentration of 2-20 μM; the ammonium formate buffer solution, the ammonium acetate buffer solution, and the ammonium citrate buffer solution have a final concentration of 0.2-20 mM, respectively; in the ammonium acetate and EDTA buffer solution, ammonium acetate has a final concentration of 0.2-20 mM, and EDTA has a final concentration of 0.2-0.8 mM; in the ammonium citrate and EDTA buffer solution, ammonium citrate has a final concentration of 0.2-20 mM, and EDTA has a final concentration of 0.2-0.8 mM; and the BSA solution has a final concentration of 10-100 μg/mL.

5. The rapid detection method according to claim 1, wherein the reaction is performed at a pH value of 3.5-4.8 and a temperature of 40-75° C. for 30-50 min.

6. The rapid detection method according to claim 1, wherein the to-be-detected sample is judged as a positive sample when the average value of the final fluorescence signal values of the incubated product is greater than the final fluorescence signal value of the negative control by plus 3 times standard deviation.

* * * * *

SEQUENCE LISTING

```
Sequence total quantity: 29
SEQ ID NO: 1            moltype = DNA  length = 15
FEATURE                 Location/Qualifiers
source                  1..15
                        mol_type = other DNA
```

-continued

```
                        organism = synthetic construct
SEQUENCE: 1
aaaaaaaaaa aaaaa                                                    15

SEQ ID NO: 2            moltype = RNA  length = 15
FEATURE                 Location/Qualifiers
source                  1..15
                        mol_type = other RNA
                        organism = synthetic construct
SEQUENCE: 2
aaaaaaaaaa aaaaa                                                    15

SEQ ID NO: 3            moltype = DNA  length = 15
FEATURE                 Location/Qualifiers
source                  1..15
                        mol_type = other DNA
                        organism = synthetic construct
SEQUENCE: 3
gctctgcagt cgctg                                                    15

SEQ ID NO: 4            moltype = RNA  length = 15
FEATURE                 Location/Qualifiers
source                  1..15
                        mol_type = other RNA
                        organism = synthetic construct
SEQUENCE: 4
gctctgcagt cgctg                                                    15

SEQ ID NO: 5            moltype = DNA  length = 32
FEATURE                 Location/Qualifiers
source                  1..32
                        mol_type = other DNA
                        organism = synthetic construct
SEQUENCE: 5
tatatatata gagagagaga gatatatata ta                                 32

SEQ ID NO: 6            moltype = RNA  length = 32
FEATURE                 Location/Qualifiers
source                  1..32
                        mol_type = other RNA
                        organism = synthetic construct
SEQUENCE: 6
tatatatata gagagagaga gatatatata ta                                 32

SEQ ID NO: 7            moltype = DNA  length = 32
FEATURE                 Location/Qualifiers
source                  1..32
                        mol_type = other DNA
                        organism = synthetic construct
SEQUENCE: 7
gcgcgcgcgc gagagagaga gagcgcgcgc gc                                 32

SEQ ID NO: 8            moltype = RNA  length = 32
FEATURE                 Location/Qualifiers
source                  1..32
                        mol_type = other RNA
                        organism = synthetic construct
SEQUENCE: 8
gcgcgcgcgc gagagagaga gagcgcgcgc gc                                 32

SEQ ID NO: 9            moltype =   length =
SEQUENCE: 9
000

SEQ ID NO: 10           moltype =   length =
SEQUENCE: 10
000

SEQ ID NO: 11           moltype =   length =
SEQUENCE: 11
000

SEQ ID NO: 12           moltype = DNA  length = 12
FEATURE                 Location/Qualifiers
source                  1..12
                        mol_type = other DNA
                        organism = synthetic construct
SEQUENCE: 12
aaaaaaaaaa aa                                                       12
```

```
SEQ ID NO: 13          moltype = DNA  length = 18
FEATURE                Location/Qualifiers
source                 1..18
                       mol_type = other DNA
                       organism = synthetic construct
SEQUENCE: 13
aaaaaaaaaa aaaaaaaa                                                18

SEQ ID NO: 14          moltype = DNA  length = 21
FEATURE                Location/Qualifiers
source                 1..21
                       mol_type = other DNA
                       organism = synthetic construct
SEQUENCE: 14
aaaaaaaaaa aaaaaaaaaa a                                            21

SEQ ID NO: 15          moltype = DNA  length = 24
FEATURE                Location/Qualifiers
source                 1..24
                       mol_type = other DNA
                       organism = synthetic construct
SEQUENCE: 15
aaaaaaaaaa aaaaaaaaaa aaaa                                         24

SEQ ID NO: 16          moltype = DNA  length = 27
FEATURE                Location/Qualifiers
source                 1..27
                       mol_type = other DNA
                       organism = synthetic construct
SEQUENCE: 16
aaaaaaaaaa aaaaaaaaaa aaaaaaa                                      27

SEQ ID NO: 17          moltype = DNA  length = 30
FEATURE                Location/Qualifiers
source                 1..30
                       mol_type = other DNA
                       organism = synthetic construct
SEQUENCE: 17
aaaaaaaaaa aaaaaaaaaa aaaaaaaaaa                                   30

SEQ ID NO: 18          moltype = DNA  length = 18
FEATURE                Location/Qualifiers
source                 1..18
                       mol_type = other DNA
                       organism = synthetic construct
SEQUENCE: 18
taaaaaaaat aaaaaaat                                                18

SEQ ID NO: 19          moltype = DNA  length = 21
FEATURE                Location/Qualifiers
source                 1..21
                       mol_type = other DNA
                       organism = synthetic construct
SEQUENCE: 19
taaataaata aataaataaa t                                            21

SEQ ID NO: 20          moltype = DNA  length = 24
FEATURE                Location/Qualifiers
source                 1..24
                       mol_type = other DNA
                       organism = synthetic construct
SEQUENCE: 20
taataataat aataataata taat                                         24

SEQ ID NO: 21          moltype = DNA  length = 18
FEATURE                Location/Qualifiers
source                 1..18
                       mol_type = other DNA
                       organism = synthetic construct
SEQUENCE: 21
taaataaata ataataat                                                18

SEQ ID NO: 22          moltype = DNA  length = 18
FEATURE                Location/Qualifiers
source                 1..18
                       mol_type = other DNA
                       organism = synthetic construct
SEQUENCE: 22
```

-continued

```
tatatatata tatataat                                                18

SEQ ID NO: 23           moltype = DNA  length = 16
FEATURE                 Location/Qualifiers
source                  1..16
                        mol_type = other DNA
                        organism = synthetic construct
SEQUENCE: 23
tatagagaga gatata                                                  16

SEQ ID NO: 24           moltype = DNA  length = 20
FEATURE                 Location/Qualifiers
source                  1..20
                        mol_type = other DNA
                        organism = synthetic construct
SEQUENCE: 24
tatatagaga gagatatata                                              20

SEQ ID NO: 25           moltype = DNA  length = 24
FEATURE                 Location/Qualifiers
source                  1..24
                        mol_type = other DNA
                        organism = synthetic construct
SEQUENCE: 25
tatatataga gagagatata tata                                         24

SEQ ID NO: 26           moltype = DNA  length = 28
FEATURE                 Location/Qualifiers
source                  1..28
                        mol_type = other DNA
                        organism = synthetic construct
SEQUENCE: 26
tatatatata gagagagata tatatata                                     28

SEQ ID NO: 27           moltype = DNA  length = 32
FEATURE                 Location/Qualifiers
source                  1..32
                        mol_type = other DNA
                        organism = synthetic construct
SEQUENCE: 27
tatatatata tagagagaga tatatatata ta                                32

SEQ ID NO: 28           moltype = DNA  length = 24
FEATURE                 Location/Qualifiers
source                  1..24
                        mol_type = other DNA
                        organism = synthetic construct
SEQUENCE: 28
tatatatata gagatatata tata                                         24

SEQ ID NO: 29           moltype = DNA  length = 36
FEATURE                 Location/Qualifiers
source                  1..36
                        mol_type = other DNA
                        organism = synthetic construct
SEQUENCE: 29
tatatatata gagagagaga gagagatata tatata                            36
```